(12) United States Patent
Dutton et al.

(10) Patent No.: US 6,362,168 B1
(45) Date of Patent: Mar. 26, 2002

(54) ANTIPARASITIC AGENTS

(75) Inventors: Christopher J. Dutton, Eastry; Stephen P. Gibson, Westbrook, both of (GB); Shih-Jen E. Lee, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 08/465,625

(22) Filed: Jun. 5, 1995

Related U.S. Application Data

(62) Division of application No. 07/647,674, filed on Jan. 25, 1991, now Pat. No. 5,702,924, which is a continuation of application No. 07/249,749, filed on Sep. 27, 1988, now abandoned.

(30) Foreign Application Priority Data

Nov. 14, 1987 (GB) .............................................. 8726730

(51) Int. Cl.[7] ........................ A61K 31/71; C07H 17/08; C07D 493/20
(52) U.S. Cl. ......................... 514/30; 514/450; 536/7.1; 549/264
(58) Field of Search ............................ 536/7.1; 514/30, 514/450; 549/264

(56) References Cited

U.S. PATENT DOCUMENTS 4,134,973 A    1/1979   Fisher et al. ................. 424/180

(List continued on next page.)

FOREIGN PATENT DOCUMENTS

| EP | 1689 | 5/1979 | |
| EP | 2615 | 6/1979 | ......... C07D/493/22 |
| EP | 214731 | 3/1987 | ......... C07D/493/22 |
| EP | 215654 | 3/1987 | |
| EP | 235085 | 9/1987 | |
| EP | 241147 | 10/1987 | ......... C07D/493/22 |
| GB | 2166436 | 5/1986 | |
| GB | 2167751 | 6/1986 | |
| GB | 2170499 | 8/1986 | |
| GB | 2176182 | 12/1986 | |

OTHER PUBLICATIONS

Schulman et al., Antimicrobial Agents and Chemotherapy 31: 744–747 (1987).
Schulman et al., Fed. Prac. 44: 931 (1985).
Schulman et al., Antibiot. 38 (11): 1494–1498 (1985).
Daum, S. J. et al., Ann. Rev. Microbiol. 33:241–265 (1979).
Schulman, M. D. et al., J. Antibiotics 34:541–549 (1986).

*Primary Examiner*—Elli Peselev
(74) *Attorney, Agent, or Firm*—Peter C. Richardson; Gregg C. Benson

(57) ABSTRACT

Compounds of the formula:

wherein
X represents a single or a double bond; $R^1$ is H or OH; provided that when X is a single bond, $R^1$ is H or OH, and when X is a double bond, $R^1$ is absent;

$R^2$ is H, $C_1$–$C_8$ alkyl, $C_2$–$C_8$ alkenyl, $C_2$–$C_8$ alkynyl, alkoxy-alkyl or alkylthioalkyl containing from 1 to 6 carbon atoms in each alkyl or alkoxy group, wherein any of said alkyl, alkoxy alkenyl or alkynyl groups may be substituted by one or more halo atoms; or a $C_3$–$C_8$ cycloalkyl or $C_5$–$C_8$ cycloalkenyl group, either of which may be substituted by methylene or one or more $C_1$–$C_4$ alkyl groups or halo atoms; or a 3 to 6 membered oxygen or sulphur containing heterocyclic ring which may be saturated, or fully or partially unsaturated and which may be substituted by one or more $C_1$–$C_4$ alkyl groups or halo atoms; or a group of the formula $SR^5$ wherein $R^5$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo, or a 3 to 6 membered oxygen or sulphur containing heterocyclic ring which may be saturated, or fully or partially unsaturated and which may be substituted by one or more $C_1$–$C_4$ alkyl groups or halo atoms;

$R^3$ is hydrogen or methyl;

and $R^4$ is H or a 4'-(alpha-L-oleandrosyl)-alpha-L-oleandrosyloxy group of the formula with the proviso that when $R^4$ and $R^1$ are both H and the double bond is absent, $R^2$ is not H or $CH_3$, are broad spectrum antiparasitic agents having utility as anthelmintics, ectoparasiticides, insecticides and acaricides.

9 Claims, No Drawings

U.S. PATENT DOCUMENTS

| | | |
|---|---|---|
| 4,156,720 A | 5/1979 | Fisher et al. .................. 424/180 |
| 4,199,569 A | 4/1980 | Chabala et al. .............. 424/180 |
| 4,200,581 A | 4/1980 | Fisher et al. .................. 424/180 |
| 4,285,963 A | 8/1981 | Arison et al. ................ 424/276 |
| 4,310,519 A | 1/1982 | Albers-Schonberg et al. .......... 424/181 |
| 4,328,335 A | 5/1982 | Mrozik ........................ 536/7.1 |
| 4,333,925 A | 6/1982 | Buhs et al. ................... 536/7.1 |
| 4,378,353 A | 3/1983 | Goegelman et al. ......... 424/181 |
| 4,423,209 A | 12/1983 | Mrozik ........................ 536/7.1 |
| 4,429,042 A | 1/1984 | Albers-Schonberg et al. .......... 435/119 |
| 4,831,016 A | 5/1989 | Mrozik ......................... 514/30 |
| 5,089,480 A * | 2/1992 | Gibson et al. ................. 514/30 |
| 5,244,879 A * | 9/1993 | Meinke et al. ................. 514/30 |

\* cited by examiner

ANTIPARASITIC AGENTS

This is a division of application Ser. No. 07/647,674, filed Jan. 25, 1991, now U.S. Pat. No. 5,702,924 which is a continuation of application Ser. No. 07/249,749, filed Sep. 27, 1988, now abandoned.

BACKGROUND OF THE INVENTION

This invention relates to antiparasitic agents and in particular to compounds related to the avermectins and milbemycins but having a novel substituent group at the 25-position and to a process for their preparation.

The avermectins are a group of broad spectrum antiparasitic agents referred to previously as the C-076 compounds. They are produced by fermenting a strain of the microorganism *Streptomyces avermitilis* ATCC 31267, 31271 or 31272 under aerobic conditions in an aqueous nutrient medium containing inorganic salts and assimilable sources of carbon and nitrogen. The morphological and cultural properties of the strains ATCC 31267, 31271 and 31272 are described in detail in British Patent Specification No. 1573955 which also describes the isolation and the chemical structure of the eight individual components which make up the C-076 complex. The milbemycins are structurally related macrolide antibiotics lacking the sugar residues at the 13-position. They are produced by fermentation, for example as described in British Patent Specification No. 1390336 and European Patent Application publication No. 0170006.

In our European Patent Application publication No. 0214731, published Mar. 18, 1987, the counterpart of U.S. application Ser. No. 886,867, filed Jul. 16, 1986, we disclose that by adding certain specified carboxylic acids, or derivatives thereof, to the fermentation of an avermectin producing organism it is possible to obtain novel compounds, related to the avermectins but having an unnatural substituent group at the 25-position in place of the isopropyl or sec-butyl group which is normally present.

The novel compounds produced are characterised in that the substituent group at the 25-position is alpha-branched i.e. the carbon atom attached to the C-25 ring position is a secondary carbon atom linked to two further carbon atoms.

In our co-pending U.S. patent application Ser. No. 107, 825, filed Oct. 13, 1987, we describe and claim new mutant strains of the microorganism *Streptomyces avermitilis* lacking branched-chain 2-oxo acid dehydrogenase activity. Said strains have been deposited in the American Type Culture Collection, Rockville, Md. under the designations *Streptomyces avermitilis* ATCC 53567 and ATCC 53568.

SUMMARY OF THE INVENTION

We have now discovered that, by using these new mutant strains of *Streptomyces avermitilis* it is possible to obtain a further range of novel avermectin derivatives, not previously obtainable, wherein the C-25 substituent is linked by an unbranched (primary) carbon atom. The novel compounds are highly active antiparasitic agents having particular utility as anthelmintics, ectoparasiticides, insecticides and acaricides. The compounds can be subjected to conventional chemical transformation reactions to obtain further novel semi-synthetic derivatives. Thus, according to the present invention there are provided compounds having the formula (I):

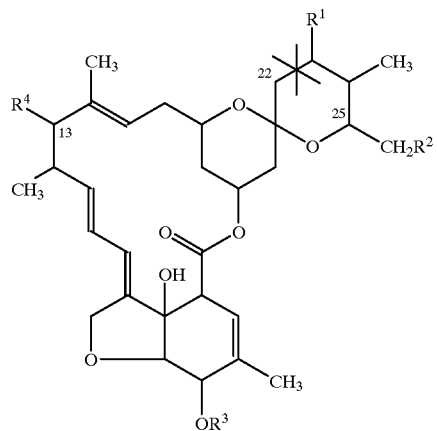

wherein

X represents a single or a double bond; $R^1$ is H or OH; provided that when X is a single bond, $R^1$ is H or OH, and when X is a double bond, $R^1$ is absent;

$R^2$ is H, $C_1$–$C_8$ alkyl, $C_2$–$C_8$ alkenyl, $C_2$–$C_8$ alkynyl, alkoxy-alkyl or alkylthioalkyl containing from 1 to 6 carbon atoms in each alkyl or alkoxy group, wherein any of said alkyl, alkoxy alkenyl or alkynyl groups may be substituted by one or more halo atoms; or a $C_3$–$C_8$ cycloalkyl or $C_5$–$C_8$ cycloalkenyl group, either of which may be substituted by methylene or one or more $C_1$–$C_4$ alkyl groups or halo atoms; or a 3 to 6 membered oxygen or sulphur containing heterocyclic ring which may be saturated, or fully or partially unsaturated and which may be substituted by one or more $C_1$–$C_4$ alkyl groups or halo atoms; or a group of the formula $SR^5$ wherein $R^5$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo, or a 3 to 6 membered oxygen or sulphur containing heterocyclic ring which may be saturated, or fully or partially unsaturated and which may be substituted by one or more $C_1$–$C_4$ alkyl groups or halo atoms;

$R^3$ is hydrogen or methyl;

and $R^4$ is H or a 4'-(alpha-L-oleandrosyl)-alpha-L-oleandrosyloxy group of the formula

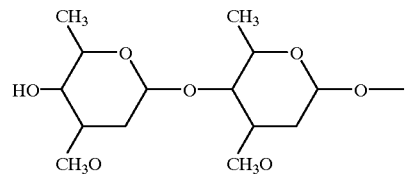

with the proviso that when $R^4$ and $R^1$ are both H and the double bond is absent, $R^2$ is not H or $CH_3$.

In the above definition, alkyl groups containing 3 or more carbon atoms may be straight or branched chain. Halo means fluoro, chloro, bromo or iodo.

The C-076 complex comprises eight distinct but closely related compounds described as C-076 A1a, A1b, A2a, A2b, B1a, B1b, B2a and B2b. The "a" series of compounds refers to the natural avermectin wherein the 25-substituent is (S)-sec-butyl and the "b" series to those wherein the 25-substituent is isopropyl. The designations "A" and "B"

refer to avermectins wherein the 5-substituent is methoxy or hydroxy, respectively, and the numeral "1" refers to avermectins wherein a double bond is present at the 22–23 position, and numeral "2" to avermectins having a hydrogen at the 22-position and hydroxy at the 23 position.

In this application, the "a" and "b" identifiers have been dropped. Identifiers A1, A2, B1 and B2 have been retained to refer to non-natural avermectins having the structural features corresponding to those of the natural avermectins as noted above.

Preferred compounds of the formula (I) are those wherein $R^4$ is 4'-(alpha-L-oleandrosyl)-alpha-L-oleandrosyloxy.

Also preferred are compounds of the formula (I) wherein $R^2$ is $SR^5$ and $R^5$ is methyl or ethyl.

In another group of preferred compounds $R^2$ is methyl, isopropyl or sec-butyl.

In a further group of preferred compounds $R^2$ is branched $C_3$–$C_8$ alkyl group substituted by one or more halo atoms, particularly 1-(trifluorome thyl) ethyl.

DETAILED DESCRIPTION OF THE INVENTION

In accordance with the invention the compounds of formula (I) wherein $R^1$ is OH and the double bond is absent or wherein the double bond is present and $R^1$ is absent and $R^4$ is 4'-(alpha-L-oleandrosyl)-alpha-L-oleandrosyloxy are prepared by fermenting a *Streptomyces avermitilis* mutant organism ATCC 53567 or 53568, as described in U.S. patent application Ser. No. 107,825, in the presence of the appropriate carboxylic acid of the formula $R^2CH_2CO_2H$, wherein $R^2$ is as previously defined, or a salt, ester, or amide thereof or oxidative precursor therefor. The acid is added to the fermentation either at the time of inoculation or at intervals during the fermentation. Production of the compounds of formula (I) may be monitored by removing samples from the fermentation, extracting with an organic solvent and following the appearance of the compound of formula (I) by chromatography, for example using high pressure liquid chromatography. Incubation is continued until the yield of the compound of formula (I) has been maximised, generally for a period of from 12 to 16 days.

A preferred level of each addition of the carboxylic acid or derivative thereof is between 0.05 and 4.0 grams per litre. The best yields of the compounds of formula (I) are obtained by gradually adding the acid to the fermentation, for example by daily additions of the acid or derivative thereof over a period of several days. The acid may be added as a salt, such as the sodium or ammonium salt, or as an ester, such as the methyl or ethyl ester or as an amide, but is preferably added as the free acid. Alternative substrates which may be used in the fermentation are derivatives which are oxidative precursors for the carboxylic acids; thus, for example suitable substrates would be alcohols of the formula $R^2 (CH_2)_n OH$ or amine derivatives of the formula $R^2 (CH_2)_n NH_2$, wherein n is 2, 4 or 6, substituted lower alkanoic acids of the formula $R^2(CH_2)_n CO_2H$ wherein n is 3 or 5 or aldehydes of the formula $R^2 (CH_2)_n CHO$ wherein n is 1, 3 or 5 and $R^2$ is as previously defined. The media used for the fermentation may be a conventional complex media containing assimilable sources of carbon, nitrogen and other trace elements.

After fermentation for a period of several days at a temperature preferably in the range of from 24 to 33° C., the fermentation broth is centrifuged or filtered and the mycelial cake is extracted with acetone or methanol. The solvent extract is concentrated and the desired product is then extracted into a water-immiscible organic solvent, such as methylene chloride, ethyl acetate, chloroform, butanol or methyl isobutyl ketone. The solvent extract is concentrated and the crude product containing the compounds of formula (I) is further purified as necessary by chromatography, for example using preparative reverse phase, high pressure liquid chromatography.

The product is generally obtained as a mixture of the compounds of formula (I) wherein $R^4$ is 4'-(alpha-L-oleandrosyl)-alpha-L-oleandrosyloxy, $R^1$ is OH and the double bond absent or $R^1$ is absent and the double bond is present and wherein $R_3$ is H or $CH_3$; however the proportions can vary depending on the particular carboxylic acid employed and the conditions used in the fermentation.

We have found that a range of carboxylic acids as defined by $R^2 CH_2CO_2H$ may be added to the fermentation to yield avermectins having a novel substituent group at the 25-position. Examples of particular acids which may be employed include the following:

methylthioacetic acid ethylthioacetic acid 3-methylbutyric acid 3-trifluoromethyl butyric acid 3-methylpentanoic acid n-butyric acid cyclopentane acetic acid thiophene-3-acetic acid and propionic acid.

In one particular and preferred aspect of the invention, the fermentation is performed in the presence of methylthioacetic acid to yield predominantly the compound of formula (I) wherein $R^1$ is OH, the double bond is absent, $R^2$ is $SCH_3$, $R^3$ is $CH_3$ and $R^4$ is 4'-(alpha-L-oleandrosyl)-alpha-4-oleandrosyloxy, referred to herein as 25-methylthiomethyl avermectin A2.

In another preferred aspect of the invention, the fermentation is performed in the presence of propionic acid to yield predominantly the compound of formula (I) wherein $R^1$ is OH, the double bond is absent, $R^2$ is $CH_3$, $R^3$ is $CH_3$ and $R^4$ is 4'(-(alpha-L-oleandrosyl)-alpha-4-oleandrosyloxy, referred to herein as 25-ethyl avermectin A2.

In a further preferred aspect of the invention the fermentation is performed in the presence of 3-methylbutyric acid to yield predominantly the compound of formula (I) wherein $R^1$ is absent, the double bond is present, $R^2$ is isopropyl, $R^3$ is H and $R^4$ is 4'-(alpha-L-oleandrosyl)-alpha-4-oleandrosyloxy, referred to herein as 25-isobutyl avermectin B1.

In a further preferred aspect of the invention, the fermentation is performed in the presence of 3-trifluoromethyl butyric acid to yield predominantly the compounds of formula (I) wherein $R^1$ is OH, the double bond is absent, $R^2$ is 1-(trifluoro-methyl)ethyl, $R^4$ is 4'-(alpha-L-oleandrosyl) alpha-4-oleandrosyloxy and $R^3$ is $CH_3$ or H referred to herein as 25-(2-trifluoromethyl-propyl)avermectin A2 and B2 respectively.

Compounds of the formula (I) wherein the double bond is present and $R^1$ is absent may alternatively be prepared from the corresponding compound of formula (I) wherein $R^1$ is OH and the double bond is absent by a dehydration reaction. The reaction is performed by first selectively protecting the hydroxyl groups at the 5 and 4" positions, e.g. as the t-butyldimethylsilyloxy acetyl derivative, then reacting with a substituted thiocarbonyl halide, such as (4-methylphenoxy)thiocarbonyl chloride, followed by heating in a high boiling point solvent, e.g. trichlorobenzene, to effect the dehydration. The product is finally deprotected to give the unsaturated compound. These steps together with appropriate reagents and reaction conditions are described in U.S. Pat. No. 4,328,335.

The compounds of formula I wherein $R^3$ is H may also be prepared from the corresponding compounds wherein $R^3$ is $CH_3$ by demethylation. This reaction is achieved by treating the 5-methoxy compound, or a suitably protected derivative thereof, with mercuric acetate and hydrolysing the resulting 3-acetoxy enol ether with dilute acid to give the 5-keto compound. This is then reduced using, for example, sodium borohydride to yield the 5-hyaroxy derivative. Appropriate reagents and reaction conditions for these steps are described in U.S. Pat. No. 4,423,209.

The compounds of-formula I wherein $R^1$ is H and the double bond is absent can be prepared from the corresponding compound wherein the double bond is present and $R^1$ is absent, by selective catalytic hydrogenation using an appropriate catalyst. For example the reduction may be achieved using tris(triphenylphosphine)rhodium (I) chloride as described in European patent application publication No. 0001689.

The compounds of formula (I) wherein $R^4$ is H are prepared from the corresponding compounds wherein $R^4$ is 4'-(alpha-L-oleandrosyl)-alpha-L-oleandrosyloxy by removing the 4'-(alpha-L-oleandrosyl)-alpha-L-oleandrose group by mild hydrolysis with an acid in an aqueous organic solvent to yield the aglycone having a hydroxy group at the 13-position; this is then halogenated, for example by reaction with a benzene esulphonyl halide, to yield the 13-deoxy-13-halo derivative which is finally selectively reduced, for example using tributyltin hydride. In order to avoid unwanted side reactions it is desirable to protect any other hydroxy groups which may be present, for example using a tert-butyldimethylsilyl group. This is then readily removed after the halogenation or reduction step by treatment with methanol containing a trace of acid. All these steps together with appropriate reagents and reaction conditions for their performance are described in European patent application publication no. 0002615.

The compounds of the invention are highly active antiparasitic agents having particular utility as anthelmintics, ectoparasiticides, insecticides and acaricides.

Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect humans including gastrointestinal parasites such as Ancylostoma, Necator, Ascaris, Strongyloides, Trichinella, Capillaria, Trichuris, Enterobius and parasites which are found in the blood or other tissues and organs such as filiarial worms and the extra intestinal stages of Strongyloides and Trichinella.

The compounds are also of value in treating, including preventing, ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars and against migratory orthopterans such as locusts.

The compounds of formula (I) are administered as a formulation appropriate to the specific use envisaged and to the particular species of host animal being treated and the parasite or insect involved. For use as an anthelmintic the compounds may be administered orally in the form of a capsule, bolus, tablet or preferably a liquid drench, or alternatively, they may be administered by injection or as an implant. Such formulations are prepared in a conventional manner in accordance with standard veterinary practice. Thus, capsules, boluses or tablets may be prepared by mixing the active ingredient with a suitable finely divided diluent or carrier, additionally containing a disintegrating agent and/or binder such as starch, lactose, talc, magnesium stearate etc. A drench formulation may be prepared by dispersing the active ingredient in an aqueous solution together with dispersing or wetting agents etc. and injectable formulations may be prepared in the form of a sterile solution which may contain other substances, for example, enough salts or glucose to make the solution isotonic with blood. These formulations will vary with regard to the weight of active compound depending on the species of host animal to be treated, the severity and type of infection and the body weight of the host. Generally for oral administration a dose of from about 0.001 to 10 mg per Kg of animal body weight given as a single dose or in divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, emulsions and the like in accordance with standard agricultural practice.

For human use the compounds are administered as a pharmaceutically acceptable formulation in accordance with normal medical practice.

The invention is illustrated by the following Examples in which Examples 1 to 8 are Examples of the preparation of compounds of the formula (I), Example 9 is an example of a drench formulation and Examples 10 and 11 illustrate the antiparasitic and insecticidal activity of the compounds.

EXAMPLE 1

25-Ethyl avermectin A2

A frozen inoculum (2 ml) of a culture of *Streptomyces avermitilis* mutant organism ATCC 53568 was inoculated into 50 mls of a medium containing starch (1 g), Pharmamedia (Trademark) (0.75 g), ardamine pH (0.25 g), and calcium carbonate (0.1 g) in a 300 ml flask and incubated at 28° C. for 2 days. This inoculum (50 ml) was transferred to a second inoculum flask (1 litre) containing starch (20 g), Pharmamedia (15 g), ardamine pH (5 g) and calcium carbonate (2 g) and incubated at 28° C. for a further 2 days. This inoculum was used to inoculate 60 litres of a medium containing starch (6 kg), magnesium sulphate (60 g), Pharmamedia (300 g), dipotassium hydrogen phosphate (60 g), ferrous sulphate (0.6 g), calcium carbonate (420 g), glutamic acid (36 g), zinc sulphate (0.06 g) and manganous sulphate (0.06 g) contained in a 60 litre fermenter. The fermentation was incubated at 29° C., with agitation at 350 r.p.m. and aeration at 60 litres per minute. Sodium propionate (140 g) was added after 96 hours and again after 192 hours (54 g). After 288 hours the mycelium was removed by filtration and extracted with acetone (2×50 litres) followed by ethyl acetate (50 litres). The acetone extract was concentrated to approximately 10 litres and extracted with the above ethyl acetate extract in three portions. The resulting ethyl acetate layers were combined and evaporated to give a brown oil (112 g).

The above oil was dissolved in 160 ml of a mixture of methanol and water (95:5) and extracted with n-hexane (2×300 ml), the hexane extracts were discarded and the methanol layer was evaporated to give a brown oil (87 g). The latter was dissolved in methylene chloride (250 ml) and stirred with silica gel (80 g) and charcoal (30 g) for 1 hour. The silica and charcoal were removed by filtration through Arbacel and the filtrate was evaporated to give a yellow oil (53 g). The latter was dissolved in methylene chloride (2.2 litres) and stirred with alumina (190 g) for two hours. The alumina was removed by filtration and the filtrate stirred with more alumina (64 g) for a further hour. The alumina was removed by filtration and the combined filter cakes from both filtrations were stirred with chloroform (1.3 litres) for 45 minutes and then the alumina was removed by filtration. The filtrate was evaporated to give a pale yellow oil (12.5 g) which was dissolved in diethyl ether and added to a column of silica gel (400 g). The column was eluted with diethyl ether and 100 ml fractions were collected. Fractions 21–28 were combined and the solvent evaporated to yield partially purified material (150 mg). The product was dissolved in methanol (0.5 ml) and chromatographed on a $C_{18}$ Zorbax ODS (Trademark, Dupont) column (21 mm×25 cm) eluting with a mixture of methanol and water (77:23) at a flowrate of 9 mls. per minute. The relevant fractions were combined and the solvent evaporated to yield the compound of formula (I) wherein $R^1$ is OH, the double bond is absent, $R^2$ and $R^3$ are both $CH_3$ and $R^4$ is 4'-(alpha-L-oleandrosyl)-alpha-L-oleandrosyloxy as a white powder, m.p 146–153° C. The structure of the product was confirmed by fast atom bombardment mass spectrometry, performed on a VG Model 7070E mass spectrometer using a sample matrix of triethylene glycol with solid sodium chloride. $(M+Na)^+$ observed at m/e 899 (theoretical 899).

Electron impact mass spectrometry was performed using a VG Model 7070F mass spectrometer. The m/e values for the principal fragments were: 570, 295, 277, 275, 183, 165, 145, 127, 113, 95 and 87.

EXAMPLE 2
25-Methylthiomethyl avermectin A2

A frozen inoculum (2 ml) of a culture of *Streptomyces avermitilis* mutant organism ATCC 53568 was inoculated into 50 mls of a medium containing starch (1 g), Pharmamedia (Trademark) (0.75 g), ardamine pH (0.25 g) and-calcium carbonate (0.1 g) in a 300 ml flask and incubated for 2 days at 28° C. on a reciprocal shaker operating at 180 r.p.m. An inoculum from this flask (25 ml) was transferred to a 3 litre flask containing 600 mls of the above medium (all ingredients pro rata) and was incubated for two days at 28° C. with agitation on a reciprocal shaker operating at 180 r.p.m. The product from this flask (40 ml) was used to inoculate a 3 litre fermenter containing 2.5 litres of a medium consisting of starch (250 g), magnesium sulphate (2.5 g), Pharmamedia (12.5 g), dipotassium hydrogen phosphate (2.5 g), ferrous sulphate (0.025 g), calcium carbonate (1.75 g), glutamic acid (1.5 g), zinc sulphate (0.0025 g), and manganous sulphate (1.5 g). This fermentation was incubated at 28° C. with agitation at 1000 r.p.m. Methylthioacetic acid (1 g) was added at 96 hours and the fermentation continued for a further 11 days. Then the mycelium was removed by filtration and extracted with acetone (2×2 litres) followed by ethyl acetate (2 litres). The acetone extract was concentrated to approximately 400 mls. and extracted with the ethyl acetate extract in three portions. The resulting ethyl acetate layers were combined and evaporated to give a brown oil (4 g) which was dissolved in diethyl ether and applied to a column of silica gel (100 g). The column was eluted with diethyl ether and 50 ml fractions were collected. Fractions 11–18 were combined and evaporated to yield partially purified material which was turther purified by chromatography on a $C_{18}$ Zorbax ODS (Trademark, Dupont) column (21 mm×25 cm) eluting with a mixture of methanol and water (77:23) at a flowrate of 9 mls. per minute. The relevant fractions were combined and evaporated to yield the compound of formula (I) wherein $R^1$ is OH, the double bond is absent, $R^2$ is $SCH_3$, $R^3$ is $CH_3$ and $R^4$ is 4'-(alpha-L-oleandrosyl)-alpha-L-oleandrosyloxy as a white powder m.p. 105–112° C. The structure of the product was confirmed by fast atom bombardment mass spectrometry was performed on a VG Model 7070E mass spectrometer using a sample matrix of triethylene glycol with solid sodium chloride. $(M+Na)^+$ observed at m/e 931 (theoretical 931).

Electron impact mass spectrometry was performed using a VG Model 7070F mass spectrometer. The m/e values for the principal fragments were: 327, 309, 243, 225, 215, 145, 127, 113, 95 and 87.

EXAMPLE 3
25-(2-Trifluoromethyl)propyl avermectins A2 and B2

The procedure of Example 1 was followed but using 3-trifluoromethyl butyric acid as substrate instead of sodium propionate. The relevant combined fractions from silica gel chromatography containing the crude A2 derivative were chromatographed on a $C_{18}$ Zorbax ODS (Trademark, Dupont) column (21 mm×25 cm) eluting with a mixture of methanol and water (75:25) at a flowrate of 9 mls/min. Fractions 167–179 were combined and evaporated to yield the compound of formula (I) wherein $R^1$ is OH, the double bond is absent, $R^2$ is 1-(trifluoromethyl)ethyl, $R^3$ is $CH_3$ and $R^4$ is 4'-(alpha-L-oleandrosyl)-L-oleandrosyloxy as a white powder, m.p. 130–136° C. The structure of the product was confirmed by fast atom bombardment mass spectrometry, performed on a VG Model 7070E mass spectrometer using a sample matrix of triethylene glycol with solid sodium chloride. $(M+Ma)^+$ observed at m/e 981 (theoretical 981).

Electron impact mass spectrometry was performed using a VG Model 7070F mass spectrometer. The m/e values for the principal fragments were: 652, 377, 359, 293. 275, 265, 257, 247, 223, 179, 145, 127, 113, 111 and 87.

The relevant fractions from silica gel chromatography containing the crude B2 derivative were combined and chromatographed on a C-18 Dynamax (Trademark Rainin) column (41.4 mm×25 cm) eluting with a mixture of methanol and water (73:27) at a flowrate of 60 mls/min. Relevant fractions were combined to yield the compound of formula (I), wherein $R^1$ is OH, the double bond is absent, $R^2$ is 1-(trifluoromethyl)ethyl, $R^3$ is H and $R^4$ is 4'-(alpha-L-oleandrosyl)-L-oleandrosyloxy as a white powder, m.p. 158–160° C. The structure of the product was confirmed by fast atom bombardment mass spectrometry performed on a VG Model 7070E mass spectrometer using a sample matrix of triethylene glycol with solid sodium chloride. $(M+Na)^+$ observed at m/e 967 (theoretical 967).

Electron impact mass spectrometry was performed using a VG Model 7070F mass spectrometer. The m/e values for the principal fragments were: 638, 377, 359, 293, 275, 265, 261, 257, 247, 223, 145, 127, 113; 111, 95 and 87.

EXAMPLE 4
25-Ethylthiomethyl avermectin A2

The procedure of Example 1 was followed but using ethylthioacetic acid as substrate instead of sodium propionate. After chromatography on a Zorbax ODS (Trademark, Dupont) column fractions 24–72 were combined to yield the compound of formula (I) wherein $R^1$ is OH, the double bond is absent, $R^2$ is ethylthio, $R^3$ is $CH_3$ and $R^4$ is 4'-(alpha-L-oleandrosyl)-L-oleandrosyloxy as a white powder, m.p. 265–270° C. (dec). The structure of the product was confirmed by fast atom bombardment mass spectrometry performed on a VG Model 7070E mass spectrometer using a sample matrix of triethylene glycol with solid sodium chloride. $(M+Na)^+$ observed at m/e 945 (theoretical 945).

Electron impact mass spectrometry was performed using a VG Model 7070F mass spectrometer. The m/e values for the principal fragments were: 616, 473, 341, 323, 257, 239, 229, 211, 187, 179, 145, 113 and 87.

EXAMPLE 5
25-Isobutyl avermectin B1

The procedure of Example 1 was followed but using 3-methylbutyric acid as substrate instead of sodium propionate. The relevant fractions from silica gel chromatography were combined and chromatographed on a $C_{18}$ Zorbax ODS (Trademark, Dupont) column (21 mm×25 cm) eluting with a mixture of methanol and water (81:19) at a flowrate of 9 mls/min. Fractions 93–98 were combined and evaporated to yield the compound of formula (I) wherein $R^1$ is absent, the double bond is present, $R^2$ is isopropyl, $R^3$ is H and $R^4$ is 4'-(alpha-L-oleandrosyl)-L-oleandrosyloxy, as a white powder, m.p. 120–123. The structure of the product was confirmed by fast atom bombardment mass spectrometry performed on a VG Model 7070E mass spectrometer using a sample matrix of triethylene glycol with solid sodium chloride. $(M+Na)^{30}$ observed at m/e 895 (theoretical 895).

Electron impact mass spectrometry was performed using a VG Model 7070F mass spectrometer. The m/e values for the principal fragments were: 565, 319, 305, 221, 193, 169, 145, 127, 113 and 87.

EXAMPLE 6
25-(2-Methylbutyl) avermectins A2 and B1

The procedure of Example 1 was followed but using 3-methylpentanoic acid as substrate instead of sodium propionate. The relevant fractions from silica gel chromatography containing the crude A2 derivative were combined and chromatographed on a C-18 Zorbax ODS (Trademark Dupont) column (21 mm×25 cm) eluting with a mixture of methanol and water (80:20) at a flowrate of 9 mls/min. Relevant fractions were combined to yield the compound of formula (I), wherein $R^1$ is OH, the double bond is absent, $R^2$ is sec-butyl, $R^3$ is methyl and $R^4$ is 4'-(alpha-L-oleandrosyl)-L-oleandrosyloxy as a white powder, m.p. 120–1250° C. The structure of the product was confirmed by fast atom bombardment mass spectrometry performed on a VG Model 7070E mass spectrometer using a sample matrix of triethylene glycol with solid sodium chloride. $(M+Na)^+$ observed at m/e 941 (theoretical 941).

Electron impact mass spectrometry was performed using a VG Model 7070F mass spectrometer. The m/e values for the principal fragments were: 337, 319, 253, 235, 225, 207, 179, 145, 113 and 87.

The relevant fractions from silica gel chromatography containing the crude B1 derivative were combined and chromatographed on a C-18 Ultrasphere (Trademark Beckman) column (10 mm×25 cm) eluting with a mixture of methanol and water (85:15) at a flowrate of 4 mls//min.

Relevant fractions were combined to yield the compound of formula (I), wherein $R^1$ is H, the double bond is present, $R^2$ is sec-butyl, $R^3$ is H and $R^4$ is 4'-(alpha-L-oleandrosyl)-L-oleandrosyloxy as a white powder, m.p. 158–164° C. The structure of the product was confirmed by fast atom bombardment mass spectrometry performed on a VG, Model 7070E mass spectrometer using a sample matrix of triethylene glycol with solid sodium chloride. $(M+Na)^+$ observed at m/e 909 (theoretical 909).

Electron impact mass spectrometry was performed using a VG Model 7070F mass spectrometer. The m/e values for the principal fragments were: 319, 235, 207, 183, 145, 113, 95 and 87.

EXAMPLE 7
25-n-Propyl avermectin A2

The procedure of Example 1 was followed but using n-butyric acid as substrate instead of sodium propionate. The relevant fractions from silica gel chromatography were combined and chromatographed on a C-18 Dynamax (Trademark Rainin) column (41.4 mm×25 cm) eluting with a gradient of methanol and water from (75:25) to (100:0) over 170 minutes at a flowrate of 40 mls/min. One minute fractions were collected and fractions 36 and 37 were combined to yield the compound of formula (I), wherein $R^1$ is OH, the double bond is absent, $R^2$ is ethyl, $R^3$ is methyl and $R^4$ is 4'-(alpha-L-oleandrosyl)-L-oleandrosyloxy as a white powder, m.p. 150–155° C. The structure of the product was confirmed by fast atom bombardment mass spectrometry performed on a VG Model 7070E mass spectrometer using a sample matrix of triethylene glycol with solid sodium chloride. $(M+Na)+$ observed at m/e 913 (theoretical 913).

Electron impact mass spectrometry was performed using a VG Model 7070 F mass spectrometer. The m/e values for the principal fragments were: 584, 309, 291, 225, 207, 197, 179, 145, 113 and 87.

EXAMPLE 8
25-Cyclopentylmethyl avermectins B1 and B2

The procedure of Example 1 was followed but using cyclopentane acetic acid instead of sodium propionate. The relevant fractions from silica gel chromatography containing the crude B1 derivative were combined and chromatographed on a C-18 Dynamax (Trademark Rainin) column (41.4 mm×25 cm) eluting with a mixture of methanol and water (84:16) at a flowrate of 60 mls/min. Relevant fractions were combined to yield a compound of formula (I), wherein $R^1$ is absent, the double bond is present, $R^2$ is cyclopentyl, $R^3$ is H and $R^4$ is 4'-(alpha-L-oleandrosyl)-L-oleandrosyloxy, as a white powder, m.p. 140–146° C. The structure of the product was confirmed by fast atom bombardment mass spectrometry performed on a VG Model 7070E mass spectrometer using a sample matrix of triethylene glycol with solid sodium chloride. $(M+Na)^+$ observed at m/e 921 (theoretical 921).

Electron impact mass spectrometry was performed using a VG Model 7070F mass spectrometer. The m/e values for the principal fragments were: 592, 331, 295, 257, 247, 218, 195, 145, 127, 113, 111, 95 and 87.

The relevant fractions from silica gel chromatogrpahy containing the crude B2 derivative were combined and chromatographed on a C-18 Ultrasphere (Trademark Beckman) column (10 mm×25 cm) eluting with a mixture of methanol and water (80:20) at a flowrate of 4 mls/min. Relevant fractions were combined to yield the compound of formula (I), wherein $R^1$ is OH, the double bond is absent, $R^2$ is cyclopentyl, $R^3$ is H and $R^4$ is 4'-(alpha-L-oleandrosyl)-

L-oleandrosyloxy as a white powder, m.p. 155–165° C. The structure of the product was confirmed by fast atom bombardment mass spectrometry performed on a VG Model 7070E mass spectrometer using a sample matrix of triethylene glycol with solid sodium chloride. (M+Na)$^+$ observed at m/e 939 (theoretical 939).

Electron impact mass spectrometry was performed using a VG Model 7070F mass spectrometer. The m/e values for the principal fragments were: 349, 335, 331, 289, 265, 261, 257, 247, 237, 219, 195, 179, 145, 127, 113, 111, 95 and 87.

EXAMPLE 9
Drench Formulation

The product of any one of the preceding Examples was dissolved in polyethylene glycol (average molecular weight 300) to give a solution containing 400 micrograms/ml for use as a drench formulation.

EXAMPLE 10
Anthelmintic Activity

Anthelmintic activity was evaluated against Caenorhabditis elegans using the in vitro screening test described by K. G. Simpkin and G. L. Coles in Parasitology, 1979, 79, 19. The products of Examples 1 to 8 all killed 100% of the worms at a well concentration of 0.1 micrograms per ml.

EXAMPLE 11
Insecticidal Activity

Activity against the larval stage of the blowfly Lucilia cuprina (Q strain) is demonstrated using a standard procedure in which first instar larvae are kept in contact with filter paper treated with test compound. The test compound is first applied to the paper as an acetone solution. The treated filter papers are then placed into tubes containing 1 ml of newborn calf serum and the first instars are added. The products of Examples 1 to 8 killed 100% of the larvae when applied to the filter paper at a level of 1 milligram per square metre.

What is claimed is:

1. A compound having the formula:

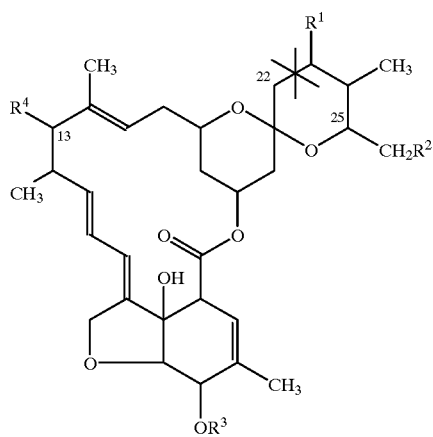

wherein
X represents a single or a double bond; $R^1$ is H or OH; provided that when X is a single bond, $R^1$ is H or OH, and when X is a double bond, $R^1$ is absent;
$R^2$ is H, $C_1$–$C_8$ alkyl, $C_2$–$C_8$ alkenyl, $C_2$–$C_8$ alkynyl, alkoxy-alkyl or alkylthioalkyl containing from 1 to 6 carbon atoms in each alkyl or alkoxy group, wherein any of said alkyl, alkoxy alkenyl or alkynyl groups may be substituted by one or more halo atoms; or a $C_3$–$C_8$ cycloalkyl or $C_5$–$C_8$ cycloalkenyl group, either of which may be substituted by methylene or one or more $C_1$–$C_4$ alkyl groups or halo atoms; or a 3 to 6 membered oxygen or sulphur containing heterocyclic ring which may be saturated, or fully or partially unsaturated and which may be substituted by one or more $C_1$–$C_4$ alkyl groups or halo atoms; or a group of the formula $SR^5$ wherein $R^5$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo, or a 3 to 6 membered oxygen or sulphur containing heterocyclic ring which may be saturated, or fully or partially unsaturated and which may be substituted by one or more $C_1$–$C_4$ alkyl groups or halo atoms;
$R^3$ is hydrogen or methyl;
and $R^4$ is H or a 4'-(alpha-L-oleandrosyl)-alpha-L-oleandrosyloxy group of the formula

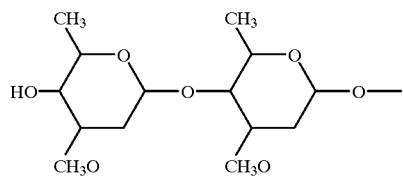

with the proviso that when $R^4$ and $R^1$ are both H and the double bond is absent, $R^2$ is not H or $CH_3$.

2. A compound as claimed in claim 1 wherein $R^4$ is 4'-(alpha-L-oleandrosyl)-alpha-L-oleandrosyloxy.

3. A compound as claimed in claim 2 wherein $R^2$ is $SR^5$ and $R^5$ is methyl or ethyl.

4. A compound as claimed in claim 2 wherein $R^2$ is methyl, isopropyl or sec-butyl.

5. A compound as claimed in claim 2 wherein $R^2$ is 1-(tri-fluoromethyl)ethyl.

6. An antiparasitic composition which comprises an effective amount of a compound of the formula (I) as claimed in claim 1 and an inert diluent or carrier.

7. A composition as claimed in claim 6 in the form of a liquid drench or an oral or injectable formulation or in the form of an animal feedstuff or a premix or supplement for addition to animal feed.

8. A method of treating insect or parasite infections or infestations in humans and animals which comprises applying an effective amount of a compound of the formula (I) as claimed in claim 1 to the organism responsible for said infection or infestation or to the location thereof.

9. A method of treating an agricultural or horticultural pest infestation which comprises applying an effective amount of a compound of the formula (I) as claimed in claim 1 to the organism responsible for said infestation or to the location thereof.

* * * * *